(12) United States Patent
Netzel

(10) Patent No.: US 10,582,944 B2
(45) Date of Patent: Mar. 10, 2020

(54) ULTRASONIC SURGICAL INSTRUMENT WITH TORQUE ASSIST FEATURE

(71) Applicant: COVIDIEN LP, Mansfield, MA (US)

(72) Inventor: Kenneth E. Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 189 days.

(21) Appl. No.: 15/903,765

(22) Filed: Feb. 23, 2018

(65) Prior Publication Data
US 2019/0262028 A1 Aug. 29, 2019

(51) Int. Cl.
*A61B 17/32* (2006.01)
*A61B 17/00* (2006.01)
(Continued)

(52) U.S. Cl.
CPC .......... *A61B 17/320092* (2013.01); *A61B 17/22012* (2013.01); *A61B 17/320068* (2013.01);
(Continued)

(58) Field of Classification Search
CPC .... A61B 17/320068; A61B 17/320092; A61B 18/1442; A61B 2017/320093; A61B 2090/031; A61B 2017/320094; A61B 2017/320069; A61B 2017/320071; A61B 2017/320082; A61B 2017/00734; A61F 9/00745
See application file for complete search history.

(56) References Cited
U.S. PATENT DOCUMENTS 1,813,902 A 7/1931 Bovie
2,235,274 A 3/1941 Trehern
(Continued)

FOREIGN PATENT DOCUMENTS

EP 0705570 A1 4/1996
EP 0908148 A1 4/1999
(Continued)

OTHER PUBLICATIONS

Extended European Search Report issued in corresponding European Application No. 19158757.5 dated Jul. 1, 2019, 9 pages.

*Primary Examiner* — Michael J Carey
*Assistant Examiner* — Alexia D Amechi

(57) ABSTRACT

An ultrasonic surgical instrument includes a housing, an ultrasonic transducer assembly, and a waveguide. The ultrasonic transducer assembly extends through a proximal opening into the housing and includes a horn disposed within the housing defining a first engagement member. The ultrasonic transducer assembly further includes an inner housing extending through the proximal opening and an outer knob disposed externally of the housing and slidably positioned about the inner housing in fixed rotational orientation relative thereto. The outer knob is selectively translatable relative to the inner housing from a proximal, unlocked position and a distal, locked position to rotationally lock the ultrasonic transducer relative to the housing. The waveguide defines a blade at a distal end and a second engagement member at a proximal end. The second engagement member is configured to releasably engage the first engagement member to thereby engage the waveguide with the ultrasonic transducer assembly.

13 Claims, 6 Drawing Sheets

(51) Int. Cl.
*A61B 17/22* (2006.01)
*A61B 18/14* (2006.01)
*A61B 90/00* (2016.01)
*A61B 17/29* (2006.01)

(52) U.S. Cl.
CPC ... *A61B 18/1442* (2013.01); *A61B 2017/0046* (2013.01); *A61B 2017/00398* (2013.01); *A61B 2017/00477* (2013.01); *A61B 2017/00734* (2013.01); *A61B 2017/2929* (2013.01); *A61B 2017/320093* (2017.08); *A61B 2017/320094* (2017.08); *A61B 2090/031* (2016.02)

(56) References Cited

U.S. PATENT DOCUMENTS

| | | |
|---|---|---|
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Nara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,828 A | 9/1998 | Lightman et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,819,298 B2 | 10/2010 | Hall et al. |
| 7,977,587 B2 | 7/2011 | Rajagopal et al. |
| 8,435,258 B2 | 5/2013 | Young et al. |
| 8,672,959 B2 | 3/2014 | Witt et al. |
| 9,017,355 B2 * | 4/2015 | Smith ............ A61B 17/320092 606/169 |
| 9,539,020 B2 | 1/2017 | Conlon et al. |
| 2001/0048855 A1 | 12/2001 | Lin |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |

(56) References Cited

U.S. PATENT DOCUMENTS

| | | |
|---|---|---|
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0171930 A1 | 9/2004 | Grimm et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2012/0078278 A1 | 3/2012 | Bales, Jr. et al. |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2017/0319229 A1 | 11/2017 | Brown et al. |

FOREIGN PATENT DOCUMENTS

| | | |
|---|---|---|
| EP | 1594209 A1 | 11/2005 |
| EP | 1707131 A1 | 10/2006 |
| EP | 2200145 A1 | 6/2010 |
| EP | 2510891 A1 | 10/2012 |
| JP | 2000506430 A | 5/2000 |
| JP | 2001112768 A | 4/2001 |
| JP | 2001514541 A | 9/2001 |
| JP | 2002518067 A | 6/2002 |
| JP | 2003502102 A | 1/2003 |
| JP | 2003285008 A | 10/2003 |
| JP | 2004129871 A | 4/2004 |
| JP | 2005278932 A | 10/2005 |
| JP | 2005296411 A | 10/2005 |
| JP | 2009538710 A | 11/2009 |
| WO | 2006087885 A1 | 8/2006 |
| WO | 2006119376 A2 | 11/2006 |
| WO | 2007047380 A2 | 4/2007 |
| WO | 2007080723 A1 | 7/2007 |

* cited by examiner

ULTRASONIC SURGICAL INSTRUMENT WITH TORQUE ASSIST FEATURE

BACKGROUND

Technical Field

The present disclosure relates to surgical instruments and, more particularly, to an ultrasonic surgical instrument including a torque assist feature to facilitate connection of a waveguide with an ultrasonic transducer.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to an end effector that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly and the end effector. Wired ultrasonic instruments operate in similar fashion except that, rather than having the generator and power source mounted on the handheld instrument itself, the handheld instrument is configured to connect to a standalone power supply and/or generator via a wired connection.

Regardless of the particular type and/or configuration of ultrasonic surgical instrument utilized, it is important to ensure proper engagement between the transducer and waveguide so that the ultrasonic energy is properly transmitted to the end effector for treating tissue therewith. Accordingly, there is a continuing need to facilitate connection of a waveguide with an ultrasonic transducer in an ultrasonic surgical instrument to ensure proper engagement therebetween.

SUMMARY

The present disclosure provides an ultrasonic surgical instrument including a torque assist feature to facilitate connection of a waveguide with an ultrasonic transducer in proper engagement with one another. As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, an ultrasonic surgical instrument is provided including a housing defining a proximal opening, an ultrasonic transducer assembly extending through the proximal opening into the housing, and a waveguide. The ultrasonic transducer assembly includes a horn disposed within the housing having a first engagement member disposed at a free distal end thereof. The ultrasonic transducer assembly further includes an inner housing extending through the proximal opening and an outer knob disposed externally of the housing and slidably positioned about the inner housing in fixed rotational orientation relative thereto. The outer knob is selectively translatable relative to the inner housing between a proximal, unlocked position, wherein the outer knob is proximally-spaced from the housing, and a distal, locked position wherein the outer knob is engaged with the housing to thereby rotationally lock the ultrasonic transducer relative to the housing. The waveguide defines a blade at a distal end and a second engagement member at a proximal end. The second engagement member is configured to releasably engage the first engagement member to thereby engage the waveguide with the ultrasonic transducer assembly.

In an aspect of the present disclosure, the housing includes a plurality of recesses defined therein and arranged about the proximal opening and the outer knob includes a plurality of fingers extending distally therefrom. Each finger is configured for engagement within one of the recesses in the distal, locked position to thereby rotationally lock the ultrasonic transducer relative to the housing.

In another aspect of the present disclosure, the ultrasonic transducer assembly further includes a biasing member disposed between the inner housing and the outer knob and configured to bias the outer knob towards the proximal, unlocked position.

In another aspect of the present disclosure, the ultrasonic transducer assembly further includes a piezoelectric stack. In such aspects, the inner housing may form at least a portion of an enclosure that encloses the piezoelectric stack therein.

In still another aspect of the present disclosure, the first and second engagement members are configured to threadingly engage one another upon relative rotation therebetween.

In yet another aspect of the present disclosure, a torque wrench assembly is operably associated with the waveguide to limit application of torque upon relative rotation between the first and second engagement members.

In still yet another aspect of the present disclosure, a generator is engaged with the ultrasonic transducer assembly to define a transducer and generator assembly that is configured to releasably couple to the housing. In such aspects, a battery assembly configured to releasably couple to the housing may be provided to power the generator for driving the ultrasonic transducer assembly.

In another aspect of the present disclosure, at least one sleeve extends distally from the housing about the waveguide. In such aspects, the blade of the waveguide extends distally from the at least one sleeve. A jaw member may be disposed at a distal end of the at least one sleeve and configured to pivot relative to the blade from an open position to a clamping position. Further, a trigger may be operably associated with the housing wherein a drive sleeve of the at least one sleeve is operably coupled between the trigger and the jaw member such that actuation of the trigger pivots the jaw member relative to the blade. In such aspects, two sleeves may be provided: the drive sleeve and a stationary support sleeve.

In another aspect of the present disclosure, a distal rotation knob is positioned distally adjacent the housing and operably coupled to the waveguide such that rotation of the distal rotation knob rotates the waveguide relative to the housing.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1:
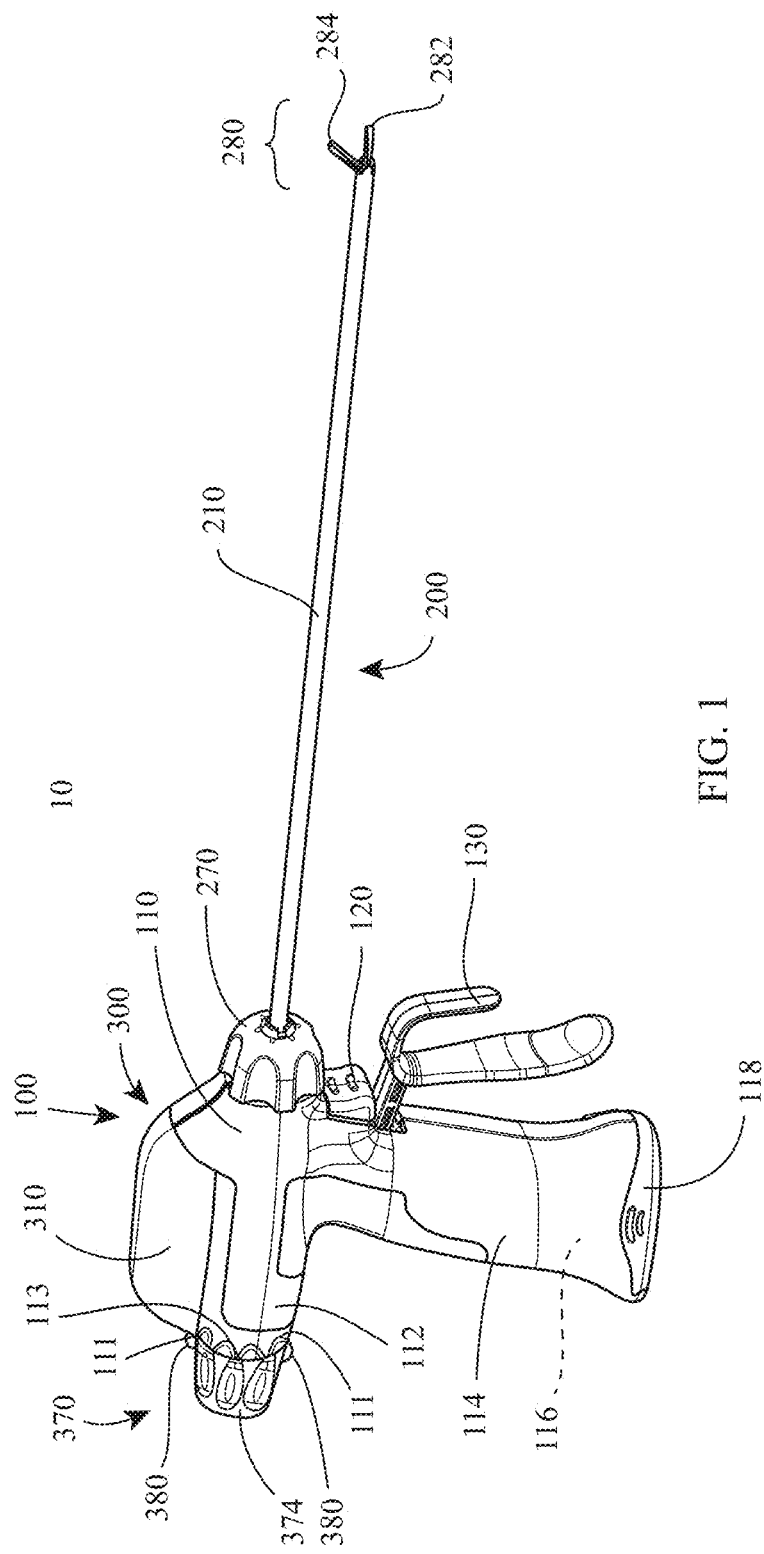
FIG. 1 is a perspective view of an ultrasonic surgical instrument provided in accordance with the present disclosure.
Figure 2:
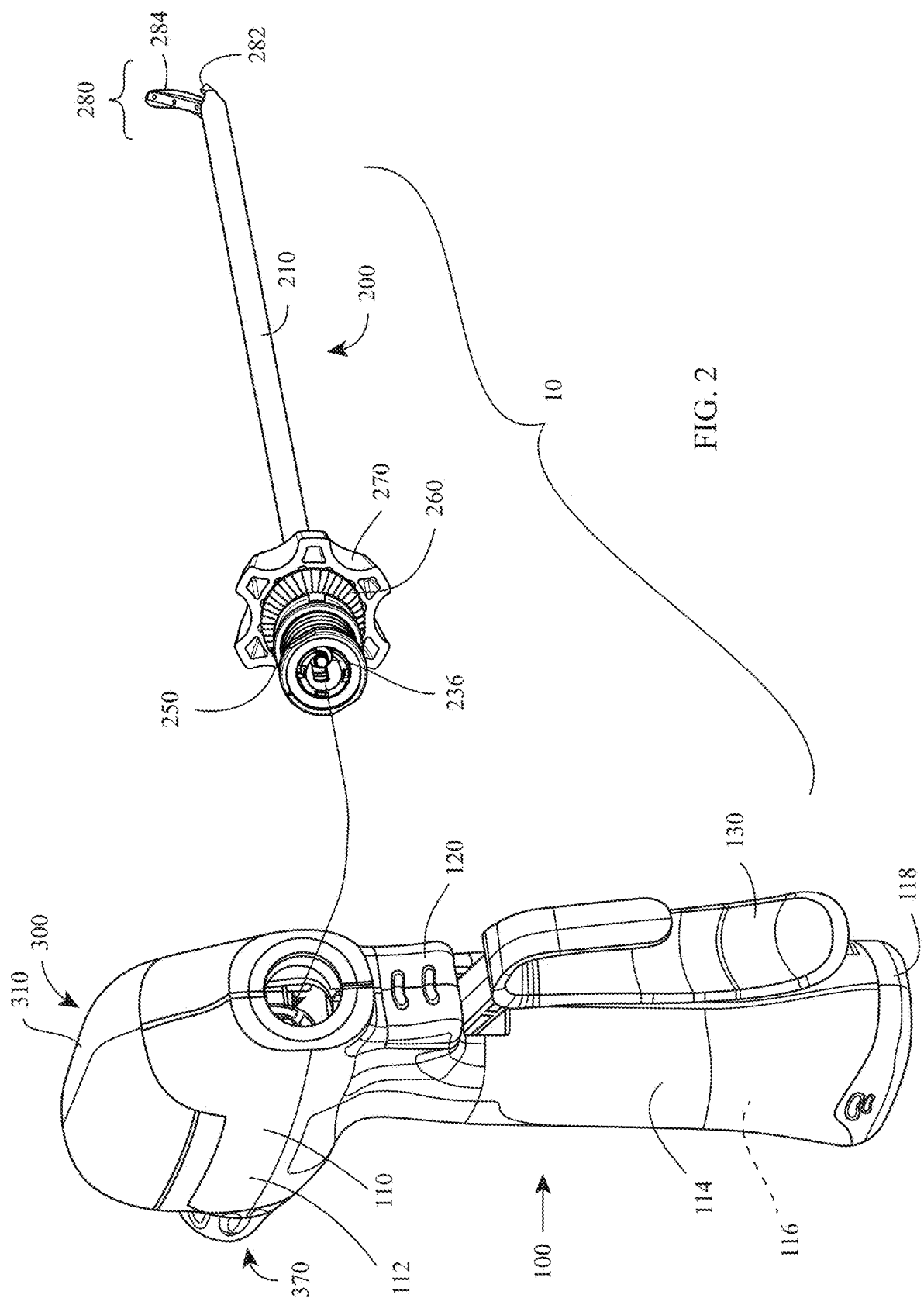
FIG. 2 is a perspective view of the ultrasonic surgical instrument of FIG. 1 with the elongated assembly separated from the handle assembly.

Referring to FIGS. 1-4, ultrasonic surgical instrument 10 includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator 310 and an ultrasonic transducer assembly 320. TAG 300 may be permanently engaged with body portion 112 of housing 110 or removable therefrom. Generator 310 includes a housing 312 configured to house the internal electronics of generator 310, and a cradle 314 configured to rotatably support ultrasonic transducer assembly 320. Alternatively, generator 310 may be remotely disposed and coupled to ultrasonic surgical instrument 10 by way of a surgical cable (not shown).

Ultrasonic transducer assembly 320 includes a piezoelectric stack 322, a horn 324, a casing 326, and a bolt 328 securing piezoelectric stack 322 between horn 324 and a proximal nut 329. Ultrasonic transducer assembly 320 further includes a proximal knob assembly 370, detailed below. Casing 326 and inner housing 372 of proximal knob assembly 370 are engaged with one another and cooperate to form an enclosure to encapsulate proximal nut 329, bolt 328, piezoelectric stack 322, and a portion of horn 324, with the remainder of horn 324 extending distally from casing 326.

A set of connectors 330 and corresponding rotational contacts 334 associated with generator 310 and ultrasonic transducer assembly 320, respectively, enable drive signals to be communicated from generator 310 to piezoelectric stack 322 of ultrasonic transducer assembly 320 to drive ultrasonic transducer assembly 320 regardless of the rotational orientation of ultrasonic transducer assembly 320. Horn 324, in turn, is configured to transmit the ultrasonic energy produced by piezoelectric stack 322 to waveguide 230 of elongated assembly 200 for transmission therealong to blade 282 of end effector 280 of elongated assembly 200, as detailed below.

Continuing with reference to FIGS. 1-4, fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In embodiments where generator 310 is remote from ultrasonic surgical instrument 10, battery assembly 400 and the configuration of fixed handle portion 114 for receiving battery assembly 400 need not be provided, as generator 310 may be powered by a standard wall outlet or other power source.

Elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, an integrated torque wrench assembly 260, a distal rotation knob 270 disposed about and forming part of integrated torque wrench assembly 260, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. During use, distal rotation knob 270 is rotatable in either direction to rotate elongated assembly 200 in either direction relative to handle assembly 100. Distal rotation knob 270 is also operably coupled to waveguide 230 via integrated torque wrench assembly 260 to facilitate attachment of waveguide 230 with horn 324 of ultrasonic transducer assembly 320, as detailed below.

Waveguide 230, as noted above, extends through inner support sleeve 220. Waveguide 230 defines a body 232 and a blade 282 extending from the distal end of body 232. Blade 282 serves as the blade of end effector 280. Waveguide 230 further includes a proximal threaded male connector 236 configured for threaded engagement within threaded female receiver 349 of horn 324 such that ultrasonic motion produced by ultrasonic transducer assembly 320 is transmitted along waveguide 230 to blade 282 for treating tissue clamping between blade 282 and jaw 284 or positioned adjacent to blade 282.

It is important to ensure that waveguide 230 and ultrasonic transducer assembly 320 are sufficiently engaged with one another and also important to inhibit over-tightening of the engagement between threaded male connector 236 and threaded female receiver 349. Integrated torque wrench assembly 260 helps ensure that waveguide 230 and ultrasonic transducer assembly 320 are sufficiently engaged while inhibiting over-tightening, as detailed below. Proximal knob assembly 370 also facilitates engagement between threaded male connector 236 and threaded female receiver 349, as also detailed below.

Figure 5A:
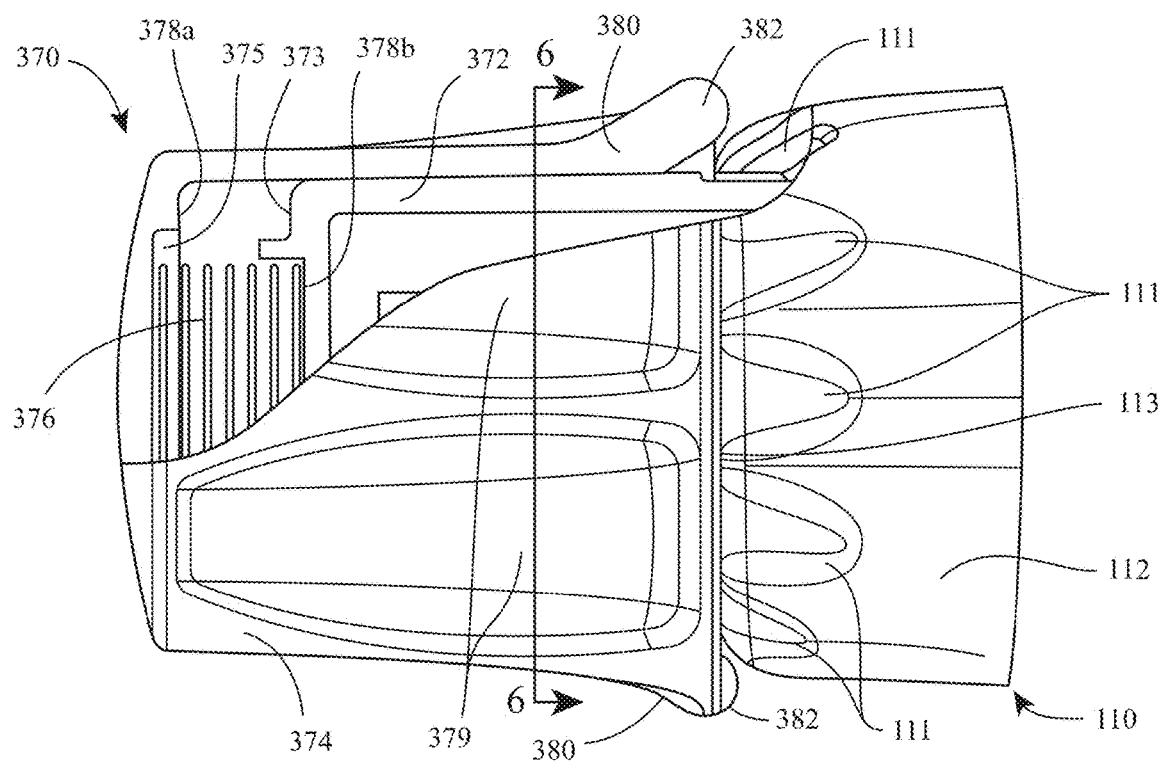
FIG. 5A is a side view of a proximal end of the ultrasonic surgical instrument of FIG. 1, wherein the proximal knob assembly thereof is disposed in an unlocked condition, with portions removed.
Figure 5B:
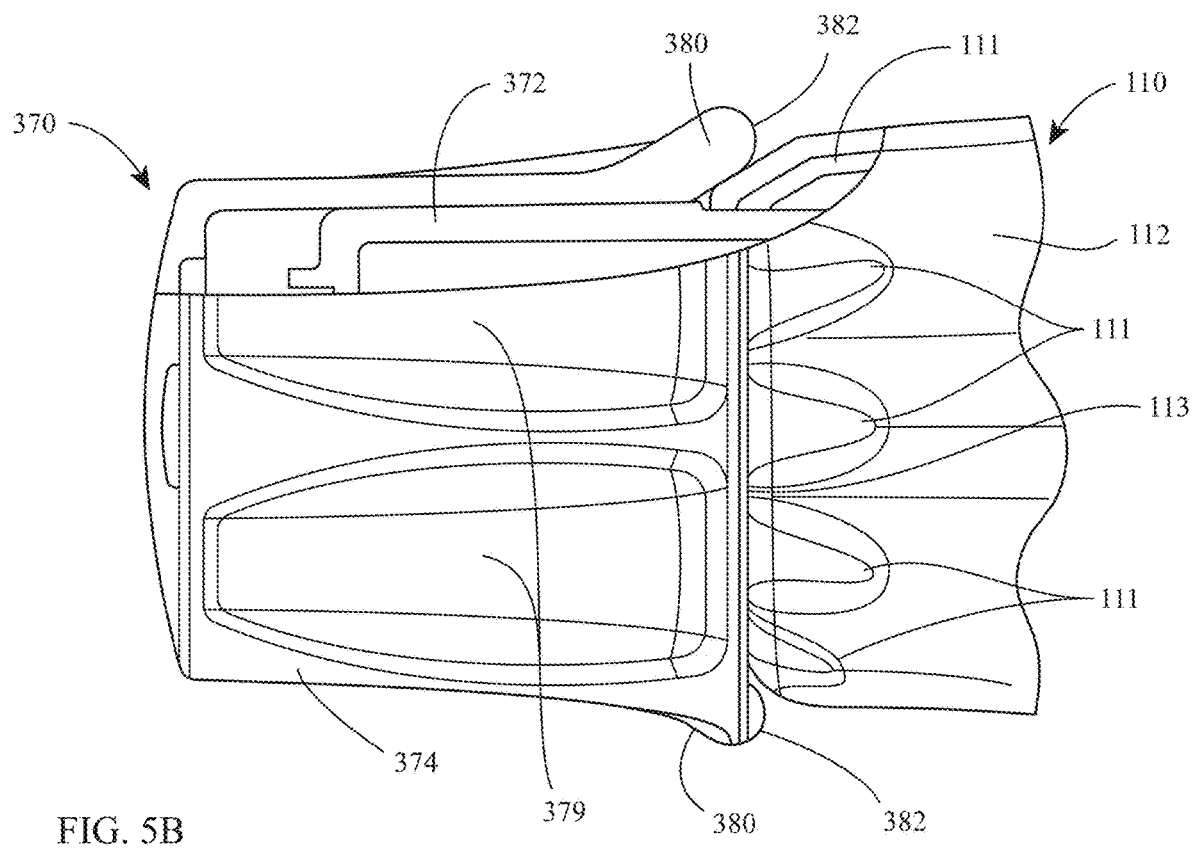
FIG. 5B is a side view of the proximal end of the ultrasonic surgical instrument of FIG. 1, wherein the proximal knob assembly thereof is disposed in a locked condition, with portions removed.
Figure 6:
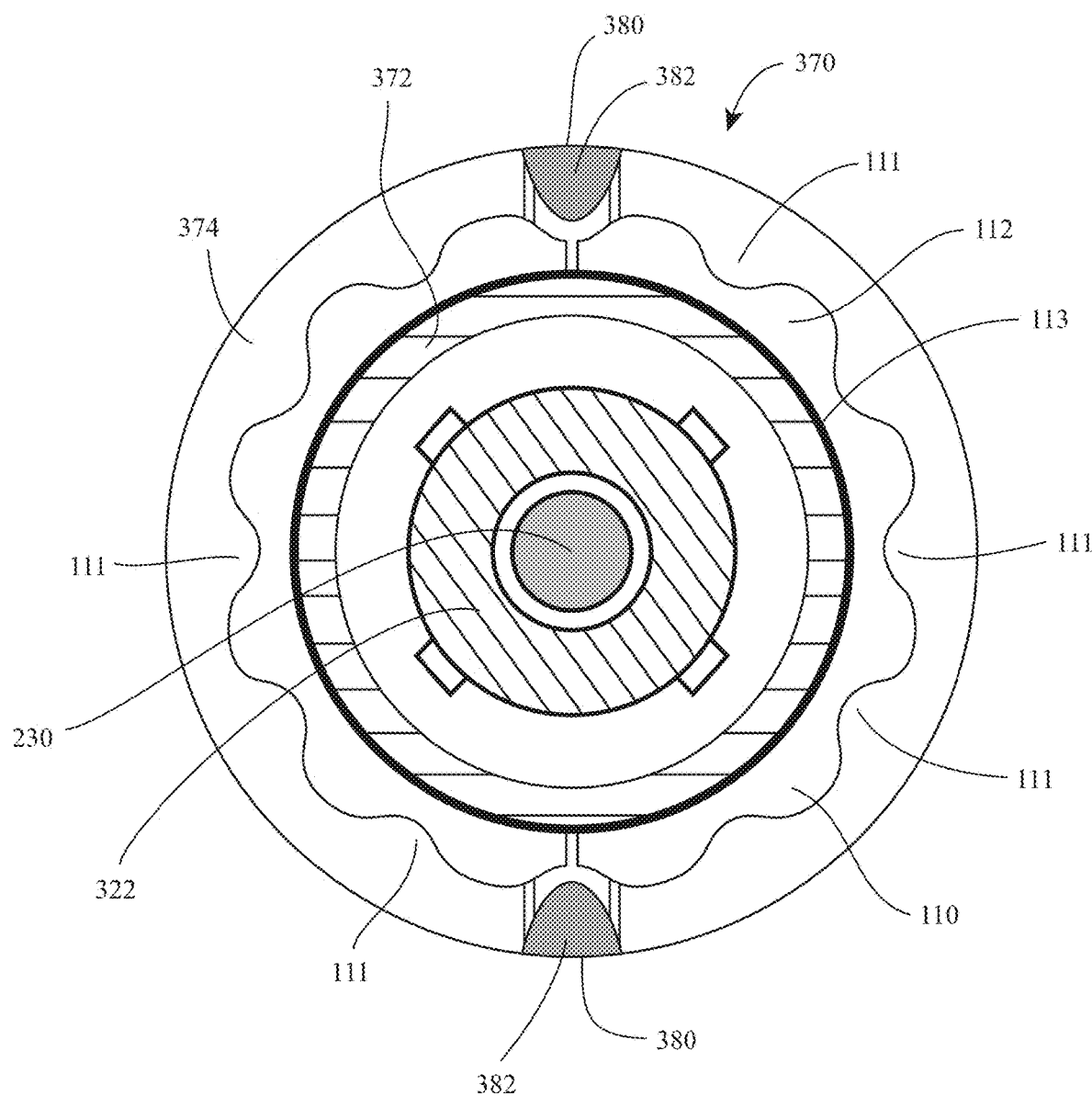
FIG. 6 is a transverse, cross-sectional view taken across section line "6-6" in FIG. 5A.

Referring to FIGS. 3-5B, proximal knob assembly 370 includes an inner housing 372, an outer rotation knob 374, and a biasing member 376, e.g., a compression coil spring. Inner housing 372 together with casing 326 of ultrasonic transducer assembly 320, as noted above, cooperate to form an enclosure to encapsulate bolt 328, proximal nut 329, piezoelectric stack 322, and a portion of horn 324 of ultrasonic transducer assembly 320, with the remainder of horn 324 extending distally from casing 326. Casing 326 and inner housing 372 are substantially fixed (within manufacturing tolerances and without regard to activation of piezoelectric stack 322 or ultrasonic motion produced thereby) relative to the other component of ultrasonic transducer assembly 320, e.g., proximal nut 329, piezoelectric stack 322, and horn 324. With particular reference to FIGS. 5A-6, outer rotation knob 374, on the other hand, is rotationally fixed relative to inner housing 372, e.g., via slidable rib-channel engagement or other suitable slidable inter-fit engagement, is disposed about inner housing 372, and is selectively translatable relative to inner housing 372 from a proximal, unlocked position, wherein outer rotation knob 374 extends further proximally from inner housing 372, and a distal, locked position, wherein outer rotation knob 374 is more-distally positioned to further surround inner housing 372. Biasing member 376 is disposed within outer rotation knob 374 and is positioned between an internal proximal surface 375 of outer rotation knob 374 and an external proximal surface 373 of inner housing 372 so as to bias outer rotation knob 374 proximally towards the proximal, unlocked position relative to inner housing 372. Recesses 378a, 378b may be defined within internal proximal surface 375 of outer rotation knob 374 and external proximal surface 373 of inner housing 372, respectively, for receipt of the ends of biasing member 376 to maintain biasing member 376 in position.

Continuing with reference to FIGS. 5A-6, outer rotation knob 374 of proximal knob assembly 370 defines a plurality of flutes 379 configured to facilitate grasping and rotation of outer rotation knob 374. Outer rotation knob 374 further includes a plurality of distally-extending fingers 380 extending from an outer annular periphery of outer rotation knob 374 at equally-spaced and/or radially-opposing positions). Fingers 380 define free distal ends 382 that are flared radially outwardly.

Figure 3:
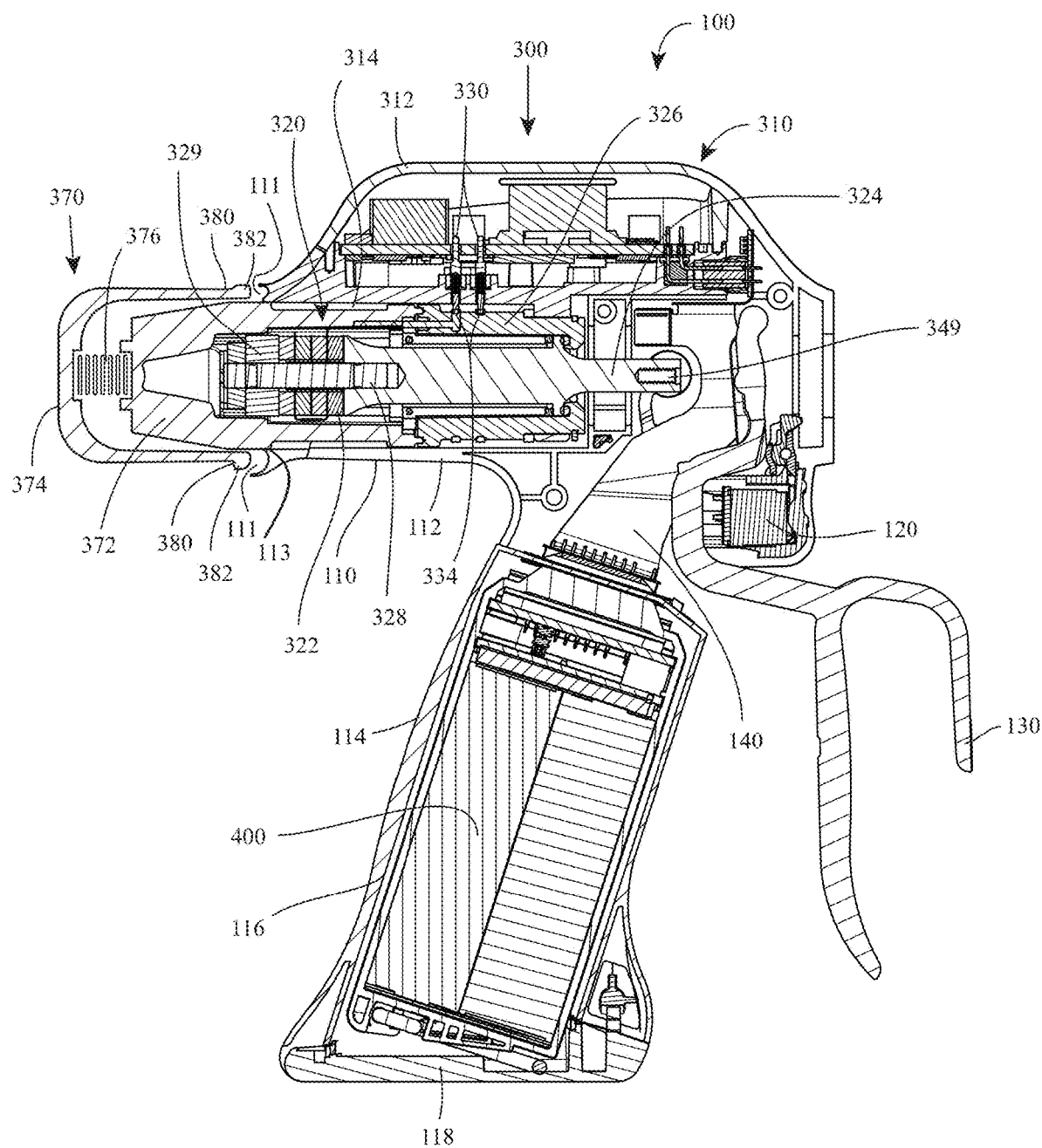
FIG. 3 is a longitudinal, cross-sectional view of a proximal portion of the ultrasonic surgical instrument of FIG. 1.
Figure 4:
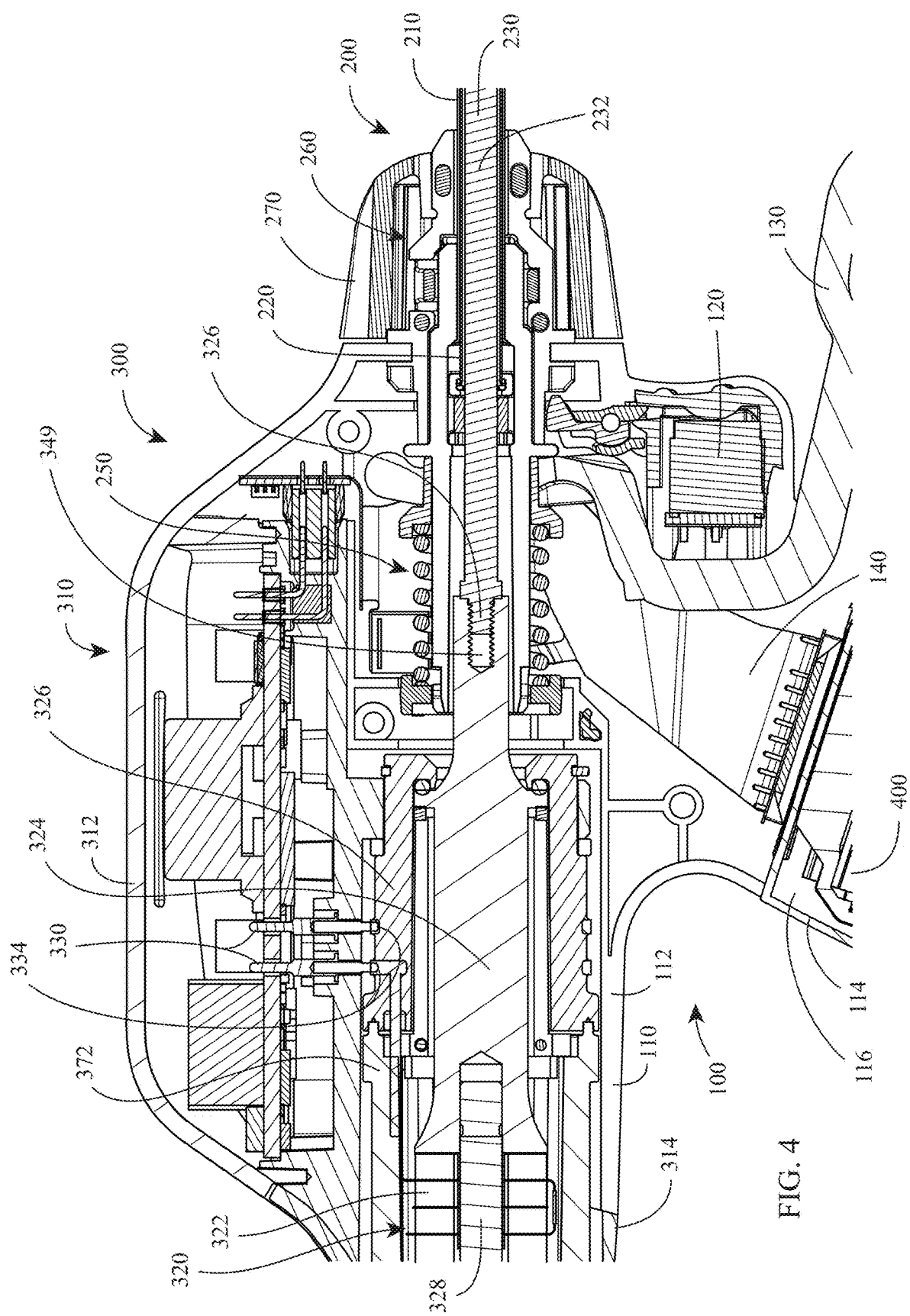
FIG. 4 is an enlarged, longitudinal, cross-sectional view of part of the proximal portion of the ultrasonic surgical instrument illustrated in FIG. 3.

With additional reference to FIGS. 1 and 3, body portion 112 of housing 110 of handle assembly 100 defines a plurality of recesses 111 surrounding the proximal opening 113 thereof through which ultrasonic transducer assembly 320 extends. The plurality of recesses 111 are radially opposed and/or equally-spaced about the annular periphery of proximal opening 113. In the proximal, unlocked position of outer rotation knob 374 (FIG. 5A), free distal ends 382 of fingers 380 are proximally-spaced from recesses 111, thus permitting rotation of outer rotation knob 374 (and, thus, ultrasonic transducer assembly 320) relative to housing 110. However, upon movement of outer rotation knob 374 to the distal, locked position (FIG. 5B), against the bias of biasing member 376, free distal ends 382 of fingers 380 are slid into engagement within recesses 111, thereby rotationally fixing outer rotation knob 374 (and, thus, ultrasonic transducer assembly 320) relative to housing 110.

With general reference to FIGS. 1-6, the assembly of ultrasonic surgical instrument 10 in preparation for use is detailed. Initially, TAG 300 is engaged with body portion 112 of housing 110 of handle assembly 100. Thereafter, or prior to engagement of TAG 300, battery assembly 400 is inserted into and compartment 116 of fixed handle portion 114 of housing 110 of handle assembly 100 and door 118 closed to retain battery assembly 400 therein. With both TAG 300 and battery assembly 400 installed in this manner, TAG 300 and battery assembly 400 are electrically coupled with one another and activation button 120 via electrical connection assembly 140.

Next, elongated assembly 200, lead by proximal connector 236 of waveguide 230 is inserted proximally into handle assembly 100 until threaded proximal connector 236 is positioned adjacent threaded female receiver 349 of horn 324 of ultrasonic transducer assembly 320. Once this position is achieved, the user urges outer rotation knob 374 of proximal knob assembly 370 distally from the proximal, unlocked position to the distal, locked position to rotationally fix ultrasonic transducer assembly 320 relative to housing 110 of handle assembly 100. While maintaining the outer rotation knob 374 in the distal, locked position (with a hand, against a rigid surface, or in any other suitable manner), the user may grasp housing 110 with one hand (e.g., the same hand maintaining outer rotation knob 374 in the distal, locked position) and grasp distal rotation knob 270 of elongated assembly 200 with the other hand. Distal rotation knob 270 of elongated assembly 200 is then rotated relative to housing 110 in a first, engagement direction, to threadingly engage threaded proximal connector 236 within threaded female receiver 349, thereby engaging waveguide 230 and ultrasonic transducer assembly 320 with one another.

Distal rotation knob 270 is rotated relative to housing 110 to achieve sufficient engagement between waveguide 230 and ultrasonic transducer assembly 320. Once sufficient engagement is achieved, integrated torque wrench assembly 260 slips, inhibiting further application or torque to the engagement between waveguide 230 and ultrasonic transducer assembly 320. Upon this slipping of integrated torque wrench assembly 260, an audible and/or tactile "click" is produced indicating to the user that sufficient engagement of waveguide 230 and ultrasonic transducer assembly 320 has been achieved. Thereafter, outer rotation knob 374 may be released, allowing outer rotation knob 374 to return under bias to the proximal, unlocked position such that ultrasonic transducer assembly 320 is permitted to rotation relative to housing 110 of handle assembly 100. Ultrasonic instrument 10 is now ready for use.

In use, ultrasonic instrument 10 is inserted into and manipulated within a surgical site such that end effector 280 is positioned adjacent tissue to be treated. If needed, end effector 280 may be rotated relative to handle assembly 100 by rotating distal rotation knob 270 (Ultrasonic transducer assembly 320 is also rotated therewith). Once positioned as desired, clamp trigger 130 may be actuated to pivot jaw member 282 from the open position towards the clamping position to clamp tissue to be treated between jaw member 282 and blade 234. As detailed above, drive assembly 250 functions to limit the clamping pressure applied to grasped tissue to a particular clamping pressure or a clamping pressure within a particular clamping pressure range.

With tissue sufficiently clamped between jaw member 282 and blade 234, activation button 120 may be activated in either the "LOW" power mode or the "HIGH" power mode to initiate the supply power from battery assembly 400 to TAG 300 for driving ultrasonic transducer assembly 320 to, in turn, transmit ultrasonic mechanical motion along waveguide 230 to blade 234 for treating tissue therewith, in either the "LOW" power mode or the "HIGH" power mode.

Once tissue(s) is sufficiently treated, ultrasonic surgical instrument 10 is withdrawn from the surgical site. Thereafter, elongated assembly 200 is disengaged from handle assembly 100 in a similar manner as the engagement thereof, detailed above, except that distal rotation knob 270 is rotated in a second, opposite, disengagement direction, to disengage threaded proximal connector 236 from threaded female receiver 349. Once disengaged, elongated assembly 200 is removed from handle assembly 100 and either or both are discarded or sterilized for subsequent use. TAG 300 and battery assembly 400 are removed from handle assembly 100 and sterilized, cleaned, charged, and/or otherwise conditions for subsequent use.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
    a housing defining a proximal opening;
    an ultrasonic transducer assembly extending through the proximal opening into the housing, the ultrasonic transducer assembly including a horn disposed within the housing, the horn having a first engagement member disposed at a free distal end thereof, the ultrasonic transducer assembly further including an inner housing extending through the proximal opening and an outer knob disposed externally of the housing and slidably positioned about the inner housing in fixed rotational orientation relative thereto, the outer knob selectively translatable relative to the inner housing between a proximal, unlocked position, wherein the outer knob is proximally-spaced from the housing, and a distal, locked position wherein the outer knob is engaged with the housing to thereby rotationally lock the ultrasonic transducer relative to the housing; and
    a waveguide defining a blade at a distal end and a second engagement member at a proximal end, the second engagement member configured to releasably engage the first engagement member to thereby engage the waveguide with the ultrasonic transducer assembly.

2. The ultrasonic surgical instrument according to claim 1, wherein the housing includes a plurality of recesses defined therein and arranged about the proximal opening, and wherein the outer knob includes a plurality of fingers extending distally therefrom, each finger configured for engagement within one of the recesses in the distal, locked position to thereby rotationally lock the ultrasonic transducer relative to the housing.

3. The ultrasonic surgical instrument according to claim 1, wherein the ultrasonic transducer assembly further includes a biasing member disposed between the inner housing and the outer knob, the biasing member configured to bias the outer knob towards the proximal, unlocked position.

4. The ultrasonic surgical instrument according to claim 1, wherein the ultrasonic transducer assembly further includes a piezoelectric stack, and wherein the inner housing forms at least a portion of an enclosure that encloses the piezoelectric stack therein.

5. The ultrasonic surgical instrument according to claim 1, wherein the first and second engagement members are configured to threadingly engage one another upon relative rotation therebetween.

6. The ultrasonic surgical instrument according to claim 5, further comprising at torque wrench assembly operably associated with the waveguide to limit application of torque upon relative rotation between the first and second engagement members.

7. The ultrasonic surgical instrument according to claim 1, further comprising a generator engaged with the ultrasonic transducer assembly to define a transducer and generator assembly, the transducer and generator assembly configured to releasably couple to the housing.

8. The ultrasonic surgical instrument according to claim 7, further comprising a battery assembly configured to releasably couple to the housing, the battery assembly configured to power the generator for driving the ultrasonic transducer assembly.

9. The ultrasonic surgical instrument according to claim 1, further comprising at least one sleeve extending distally from the housing and disposed about the waveguide, wherein the blade of the waveguide extends distally from the at least one sleeve.

10. The ultrasonic surgical instrument according to claim 9, further comprising a jaw member disposed at a distal end of the at least one sleeve, the jaw member configured to pivot relative to the blade from an open position to a clamping position.

11. The ultrasonic surgical instrument according to claim 10, further comprising a trigger operably associated with the housing, wherein a drive sleeve of the at least one sleeve is operably coupled between the trigger and the jaw member such that actuation of the trigger pivots the jaw member relative to the blade.

12. The ultrasonic surgical instrument according to claim 11, wherein the at least one sleeve includes two sleeves: the drive sleeve and a stationary support sleeve.

13. The ultrasonic surgical instrument according to claim 1, further comprising a distal rotation knob positioned distally adjacent the housing and operably coupled to the waveguide, wherein rotation of the distal rotation knob rotates the waveguide relative to the housing.

\* \* \* \* \*